(12) United States Patent
Gao et al.

(10) Patent No.: US 7,655,404 B2
(45) Date of Patent: Feb. 2, 2010

(54) METHOD AND DEVICE FOR DETECTION OF NUCLEIC ACIDS AND/OR POLYPEPTIDES

(75) Inventors: Zhiqiang Gao, Singapore (SG); Hong Xie, Singapore (SG); Yuan Hong Yu, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 148 days.

(21) Appl. No.: 11/568,154

(22) PCT Filed: Apr. 29, 2004

(86) PCT No.: PCT/SG2004/000113

§ 371 (c)(1), (2), (4) Date: Oct. 20, 2006

(87) PCT Pub. No.: WO2005/106034

PCT Pub. Date: Nov. 10, 2005

(65) Prior Publication Data

US 2007/0248964 A1    Oct. 25, 2007

(51) Int. Cl.
*C12Q 1/68*  (2006.01)
*G01N 33/53* (2006.01)

(52) U.S. Cl. ............................................. 435/6; 435/7.1
(58) Field of Classification Search ................... 435/6, 435/7.1
See application file for complete search history.

(56) References Cited

U.S. PATENT DOCUMENTS

2003/0082601 A1  5/2003  Dill
2004/0048241 A1  3/2004  Freeman et al.

FOREIGN PATENT DOCUMENTS

WO          0165246 A1      9/2001
WO          03042396 A2     5/2003
WO     WO 03/042396   *    5/2003

OTHER PUBLICATIONS

Xie et al (Nucleic Acids Research, 2004, 32(2):1-7).*
Dequaire et al (Anal. Chem, 2002, 74:4370-4377).*
Kainu et al (Cancer Research, Jul. 1996, 56:2912-2915).*
Bardea et al., "Amplified microgravimetric quartz-crystal-microbalance analyses of oligonucleotide complexes: a route to a Tay-Sachs biosensor device", Chemical Commununications, 1998, pp. 839-840.
Boon et al., "Mutation detection by electrocatalysis at DNA-modified electrodes", Nature Biotechnology, 2000, vol. 18: 1096-1100.
Caruana et al., "Enzyme-Amplified Amperometric Detection of Hybridization and of a Single Base Pair Mutation in an 18-Base Oligonucleotide on a 7-um-Diameter Microelectrode", Journal of the American Chemical Society, 1999, vol. 121 (4): 769-774.
Chan et al., "Nonisotopic Quantitation of mRNA Using a Novel RNase Protection Assay: Measurement of erbB-2 mRNA in Tumor Cell Lines", Analytical Biochemistry, 1996, vol. 242 (2): 214-220.
Fotin et al., "Parallel thermodynamic analysis of duplexes on oligodeoxyribonucleotide microchips", Nucleic Acids Research, 1998, vol. 26 (6): 1515-1521.
Jordan et al., "Surface Plasmon Resonance Imaging Measurements of DNA Hybridization Adsorption and Streptavidin/DNA Multilayer Formation at Chemically Modified Gold Surfaces", Analytical Chemistry, 1997, vol. 69 (24): 4939-4947.
Kelley et al., "Electrochemistry of Methylene Blue Bound to a DNA-Modified Electrode", Bioconjugate Chemical, 1997, vol. 8 (1): 31-37.
Kelley et al., "Single-base mismatch detection based on charge transduction through DNA", Nucleic Acids Research, 1999, vol. 27 (24): 4830-4837.
Lay et al., "cis-BIS(2,2'-Bipyridine-N,N') Complexes of Ruthenium(III)/(II) and Osmium(III)/(II)", Inorganic Syntheses, 1986, vol. 24: 291-299.
Martin et al., "Linking Gene Expression Patterns to Therapeutic Groups in Breast Cancer", Cancer Research, 2000, 60: 2232-2238.
Patolsky et al., "Amplified Microgravimetric Quartz-Crystal-Microbalance Assay of DNA Using Oligonucleotide-Functionalized Liposomes or Biotinylated Liposomes", Journal of the American Chemical Society, 2000, vol. 122 (2): 418-419.
Rodriguez et al., "Electrochemical Studies of the Interaction of Metal Chelates with DNA. 4. Voltammetric and Electrogenerated Chemiluminescent Studies of the Interaction of Tris(2,2'-bipyridine)osmium(II) with DNA", Analytical Chemistry, 1990, vol. 62(24): 2658-2662.

(Continued)

*Primary Examiner*—Sean E Aeder
(74) *Attorney, Agent, or Firm*—Caesar, Rivise, Bernstein, Cohen & Pokotilow, Ltd.

(57) ABSTRACT

A method for the detection and/or quantification of at least one target nucleic acid or target polypeptide in a sample of nucleic acids or polypeptides comprising the steps of: a) providing a sample comprising nucleic acids or polypeptides; b) labeling the nucleic acids or polypeptides with a ligand conjugate, the ligand conjugate comprising a first element binding to the nucleic acids or polypeptides and a second element which is a capture ligand; c) contacting the nucleic acid-ligand conjugates or polypeptide-ligand conjugates with at least one capture probe, the capture probe hybridizing with or binding to at least one target nucleic acid or target polypeptide; d) adding i) an oxidoreductase enzyme, wherein the oxidoreductase enzyme is recognized by the capture ligand, or ii) a complex comprising an oxidoreductase enzyme bound to a capture receptor, the capture receptor capable of binding to the capture ligand; e) adding a redox polymer, the redox polymer binding to the oxidoreductase enzyme, thereby resulting in the transfer of electrons from the enzyme via the redox polymer to an electrode surface; and f) detecting and/or quantifying the presence of the target nucleic acid(s) or target polypeptide(s).

30 Claims, 10 Drawing Sheets

OTHER PUBLICATIONS

Sullivan et al., "Mixed Phosphine 2,2'-Bipyridine Complexes of Ruthenium", Inorganic Chemistry, 1978, vol. 17 (12): 3334-3341.

Totzke et al., "Competitive reverse transcription/polymerase chain reaction for the quantification of p53 and mdm2 mRNA expression", Molecular and Cellular Probes, 1996, vol. 10 (6): 427-433.

Trudeau et al., "Reagentless Mediated Laccase Electrode for the Detection of Enzyme Modulators", Analytical Chemistry, 1997, vol. 69 (5): 882-886.

Xie et al., "Amperometric Detection of Nucleic Acid at Femtomolar Levels with a Nucleic Acid/Electrochemical Activator Bilayer on Gold Electrode", Anal. Chem., vol. 76 (2004), pp. 1611-1617.

Xie et al., "Highly sensitive amperometric detection of genomic DNA in animal tissues", Nucleic Acids Research, vol. 32, No. 2 (2004), pp. 1-7.

Wang, "Survey and Summary From DNA biosensors to gene chips", Nucleic Acids Research, 2000, vol. 28 (16): 3011-3016.

Zhang et al., "Enzyme-Amplified Amperometric Detection of 3000 Copies of DNA in a 10-uL Droplet at 0.5fM Concentration", Analytical Chemistry, 2003, vol. 75(13): 3267-3269.

Search Report for Taiwanese Patent Application 094113677.

Cottrez et al., "Quantitive PCR: validation of the use of a multispecific internal control", Nucleic Acids Research, vol. 22, No. 13 (1994), pp. 2712-2713.

Decher, "Fuzzy Nanoassemblies: Toward Layered Polymeric Multicomposites", Science, vol. 277 (1997), pp. 1232-1237.

International Search Report relating to PCT/SG 2004/000113.

Gao et al., "Electrodeposition of Redox Polymers and Co-Electrodeposition of Enzymes by Coordinative Crosslinking", Angew. Chem. Int. Ed., vol. 41, No. 5 (2002).

\* cited by examiner

A)

Hydrophobic Film
Ag/AgCl
Adhesive Spacer
Gold
Glass Slide

B)

METHOD AND DEVICE FOR DETECTION OF NUCLEIC ACIDS AND/OR POLYPEPTIDES

FIELD OF THE INVENTION

This invention relates to methods of detecting and/or quantifying the expression of at least one target gene of interest. In particular, this invention is useful in the simultaneous detection and/or quantification of a plurality of target genes, in particular, selected expressed genes. The invention also provides a device for carrying out the detection and/or quantification.

BACKGROUND OF THE INVENTION

The most commonly used methods for the quantification of gene expression include northern blotting (Watson, J., et al., Recombinant DNA, 2$^{nd}$ Edn. W.H. Freeman and Company, New York, 1992), ribonuclease protection (Chan, S. D. H, et al., Anal. Biochem., 242, 214, 1996) and reverse transcription-polymerase chain reaction (RT-PCR)(Cottrez, F., et al., Nucleic Acids Res., 22, 2712, 1994; Totze, G., et al., Mol. Cell. Probes, 10, 427, 1996). The first two methods require 10-100 µg of mRNA and can detect single mRNA molecules at $10^6$-$10^7$ copy levels. Such quantities can be easily isolated from bulk tissues, but if one has to quantify a number of genes in limited amounts of sample or has a need to separate only certain types of cells for analysis, northern blotting and ribonuclease protection techniques are not feasible. RT-PCR can theoretically amplify a single nucleic acid molecule by millions of times and thus could be very useful for very small sample sizes. However, RT-PCR amplification tends to introduce contamination. It also requires considerable optimization of primer sets and sample pretreatments, therefore, prolonging assay time. More frequently, different amounts of mRNA sequences in a starting mRNA mixture may not be represented at the same level in the final RT-PCR products due to selective and non-linear target amplifications. Incomplete denaturation of RNA secondary structure during the cDNA synthesis step can also halt the polymerase, resulting in shorter cDNA copies of the target mRNA. These limitations affect the precision and quality of the resulting data, and often provide distorted information of gene expression. Multiple replicates can help to gain confidence in the results for such experiments, but that is not applicable to small or rare samples.

To circumvent the above-mentioned problems associated with RT-PCR, techniques that use a cisplatin-digoxigenin derivative conjugate to directly label nucleic acid molecules have recently been developed (Hoevel T., et al, Biotechniques, 27(5):1064-7, 1999). The key advantage of the direct nucleic acid labeling methodology is that it is simple, fast and less perturbing to the nucleic acid molecules. The resulting labeled nucleic acid allows a greater accuracy in the identification of differentially expressed genes. However, the quantification of gene expression has proven to be difficult owing to the limited sensitivity of the existing nucleic acid detection techniques.

Usually micrograms of mRNA is needed for quantitative purposes (Hoevel T., et al., Biotechniques, 27(5):1064, 1999; Boon, E. M., et al., Nat. Biotechnol., 18, 1096, 2000). Sensitive gene detection is one of the challenges in current and future molecular diagnostics.

Recent advances in developing bioelectronic DNA analysis systems open up new opportunities for molecular diagnostics and have attracted substantial research efforts (Boon, E. M., et al., Nat. Biotechnol., 18, 1096, 2000; Rodriguez, M. & Bard, A. J. Anal. Chem., 62, 1658, 1990). Optical (Jordan, C. E., et al., Anal. Chem., 69, 4939, 1997; Fotin, A. V., et al., Nucleic Acids Res., 26, 1515, 1998), electrochemical (Kelley, S. O., et al., Bioconjug. Chem., 8, 31, 1997; Kelly, S. O., et al., Nucleic Acids Res., 27, 4830, 1999), and microgravimetric and quartz-crystal microbalance (Bardea, A., et al., Chem. Commun., 839, 1998; Wang, J., Nucleic Acids Res., 28, 3011, 2000), transduction methods have been reported for the detection of DNA hybridization events. Amplified electronic transduction of nucleic acid recognition events (Caruana, D. J. and Heller, A., J. Am. Chem. Soc., 121, 769, 1999; Patolsky, F., et al., Chem. Int., 40, 2261, Ed. 2001; Patolsky, F., et al., J. Am. Chem. Soc., 122, 418, 2000; Zhang, Y., et al., Anal. Chem., 75, 3267, 2003) has also been addressed recently. The inherent miniaturization of electrochemical biosensors and their compatibility with advanced semiconductor technologies promise to provide a simple, accurate and inexpensive platform for an early diagnosis of genetic diseases. Despite the enormous progress made in electrochemical nucleic acid biosensors in the past 5 years, in order to be one step closer to the market several important hurdles need to be overcome. The first is to test the biosensors on genomic nucleic acid from real-world samples (Lay, P. A., et al., Inorg. Synth., 24, 291, 1986). So far, most of the electrochemical biosensors start with relatively short synthetic oligonucleotides, or with a round of PCR amplification. Another challenge is to multiplex the electrochemical biosensors and their fabrication into useful sensor arrays. Typically, arrays of 30 to 100 are needed for diagnostic purposes. For example, breast cancer screening requires testing for 20-30 cancer marker genes in addition to positive and negative controls (Drummond, T. G., et al., Nat. Biotechnol., 21, 1192, 2003).

Accordingly, there is a need in the art for the development of improved and efficient methods for the identification and/or analysis of small amounts of nucleic acids. In particular, there is a need for improved and efficient methods for the direct identification and/or analysis of target genes in the total mRNA present in a sample.

SUMMARY OF THE INVENTION

The present invention addressess the needs of the prior art and provide a simple, rapid and ultrasensitive method and device for the detection and/or quantification of target nucleic acids. The method and device according to the invention can also be applied to the detection and/or quantification of target proteins.

According to a first aspect, the invention provides a method for the detection and/or quantification of at least one target nucleic acid or target polypeptide in a sample of nucleic acids or polypeptides comprising the steps of:
 a) providing a sample comprising nucleic acids or polypeptides;
 b) labelling the nucleic acids or polypeptides with a ligand conjugate, the ligand conjugate comprising a first element binding to the nucleic acids or polypeptides and a second element which is a capture ligand;
 c) contacting the nucleic acid-ligand conjugates or polypeptide-ligand conjugates with at least one capture probe, the capture probe hybridising with or binding to at least one target nucleic acid or target polypeptide;
 d) adding i) an oxidoreductase enzyme, wherein the oxidoreductase enzyme is recognised by the capture ligand, or ii) a complex comprising an oxidoreductase enzyme bound to a capture receptor, the capture receptor capable of binding to the capture ligand;

e) adding a redox polymer, the redox polymer binding to the oxidoreductase enzyme, thereby resulting in the transfer of electrons from the enzyme via the redox polymer to an electrode surface; and f) detecting and/or quantifying the presence of the target nucleic acid(s) or target polypeptide(s).

The capture probe may be fixed onto an electrode surface. Alternatively, the capture probe may be free in solution and comprise means to enable it to fix to an electrode surface.

The sample of nucleic acids may be a mammal sample, for example a human or mouse sample. The sample, for example a sample of total mRNA, may be extracted from a tissue.

When the sample is a sample of nucleic acids, like mRNAs, cDNAs and/or genomic DNA, the capture probe is an oligonucleotide complementary to and capable of hybridising with at least one portion of the target nucleic acid(s).

According to a particular embodiment, the sample is a sample of total mRNA, and the capture probe fixed on the electrode surface is an oligonucleotide complementary to a portion of the target mRNA(s).

This method is referred to as the direct detection and/or quantification mRNA method.

When the sample is a sample of polypeptides, for example proteins, the capture probe may be any ligand capable of recognising and binding to the target polypeptide, for example an antibody specific for the target polypeptide.

The first element that binds to the nucleic acids or to the polypeptides may in general be a labelling agent, for example, cisplatin, platinum-linked Cyanine 3, platinum-linked Cyanine 5. The capture ligand may be any a liable (exchangeable) ligand capable of binding to the capture receptor, like biotin, digoxigenin, an antibody or antigen binding to the capture receptor, an antibody binding to the oxidoreductase enzyme, an aptamer, a protein and/or a protein receptor.

The capture receptor may be avidin, streptoavidin, anti-digoxigenin, an antigen or antibody binding to the capture ligand, an aptamer, a protein and/or a protein receptor.

According to a particular embodiment, the ligand conjugate is cisplatin-biotin and the capture receptor is avidin or streptoavidin. In particular, the complex is GOX-strep (avidin).

According to another embodiment, the oxidoreductase enzyme binds to the capture ligand, wherein the capture ligand is an antibody.

The oxidoreductase enzyme may be any enzyme suitable for the purposes of the present invention, for example an oxidase, a dehydrogenase, a mono-oxygenase, a hydroxylase, a dioxygenase, a peroxidase, a hydrogenase, or the like. The oxidase may be any oxidase suitable for the purposes of the present invention, for example, glucose oxidase (GOX), lactase oxidase (LAX), pyruvate oxidase (PYX), tyrosinase or a mixture thereof.

The redox polymer may be any redox polymer known in the art and suitable for the purposes of the present invention. For example, the redox polymer may be a redox active polymeric material, poly(vinylimidazole-co-acrylamide), poly(vinylimidazole-co-acrylamide) partially imidazole-complexed with $[Os(bpy)_2]$, $[Os(dmbpy)_2]$, $[(Osbpy)_2(im)]$, $[Os(dabpy)_2]$ and/or $[Os(bpy)_2(Mim)]$, poly[vinylpyridine Os(bis-bipyridine)$_2$Cl-co-allylamine] (PVP-Os-AA), horseradish peroxidase (HRP), ferrocene-based polymer, and/or ruthenium-based polymers.

According to a particular embodiment, the method of the invention is a diagnostic method for the detection and/or quantification of one or more target genes. The target gene may be at least one of the following: tumor protein p53 (TP53), heat-shock protein 90 (HSP90), breast cancer gene 1 (BRCA1), and/or Histone H4 (His4). The diagnostic method according to the invention may also detect and/or quantify different target genes at the same time.

The method according to the invention allows for the detection of very small amounts of nucleic acids or polypeptides. For example, when the sample is a sample of total mRNA, the method of the invention allows for the detection of target mRNA(s) within the limits of 0.10-0.95 fg.

According to another aspect, the present invention provides a device for carrying out the method of the invention.

The device consists of a sensor array. In particular, a sensor array device for the detection of target nucleic acids and/or polypeptides in a sample analyte comprising a first and second electrode separated by a spacer/insulating layer, and wherein the electrode become connected when the analyte is applied to the second electrode. The current passing through the two electrodes reflects the quantity of analyte applied. The electrode material is made of any material suitable for the purposes of the present invention. For example, the electrode material may be made of gold, platinum, glassy carbon, graphite, carbon pastes (CPE), carbon-epoxy composites for amperometry, doped diamond film, carbon nanotubes, Indium-Tin oxide, and/or any conductive materials, such as conductive polymer, doped semiconductors. In particular, the spacer/insulator layer comprises from the bottom to the top, an adhesive spacing/insulating layer, a screen-printed Ag/AgCl layer and a hydrophobic layer. Further, the support may be a glass support. The analyte may be a sample of total mRNA, a sample of cDNAs or genomic DNAs.

According to a particular aspect, the device according to the invention is integrated in a microelectromedical system (MEMS) and/or fully automated Micro Total Analysis System (μ-TAS).

According to another aspect, the invention provides a diagnostic kit comprising the following components: A) at least one capture probe i) fixed on an electrode surface, or ii) comprising the means to be able to fix to an electrode surface; B) a ligand conjugate for labelling nucleic acids or polypeptides of a sample, the ligand conjugate comprising a first element binding to the nucleic acids or polypeptides and a second element which is a capture ligand; C) i) an oxidoreductase enzyme, wherein the oxidoreductase enzyme is capable of being bound by the capture ligand, or ii) a complex comprising an oxidoreductase enzyme bound to a capture receptor, the capture receptor being capable of binding to the capture ligand; D) a redox polymer.

DETAILED DESCRIPTION OF THE INVENTION

Figure 1:
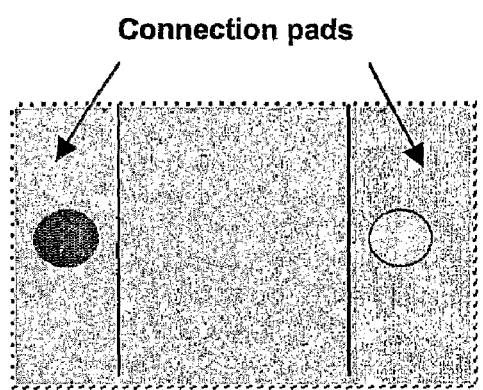
FIG. 1 (A and B): A top view (A) and an exploded view (B) of the sensor array device according to the invention.
Figure 1:
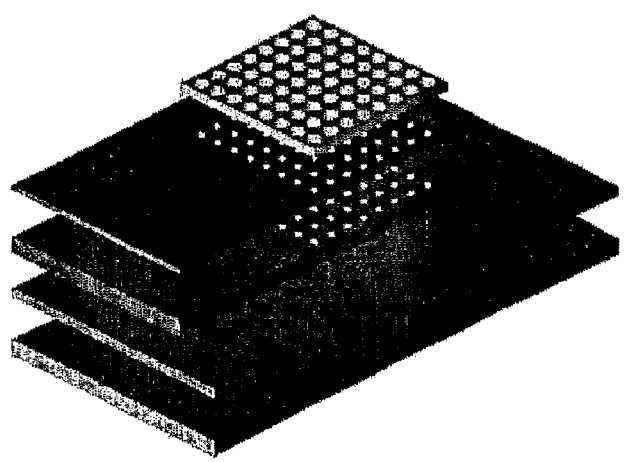

The present invention provides a simple, rapid, efficient and ultrasensitive method and device for the detection and/or quantification of target nucleic acids. The method and device according to the invention can be applied to the detection and/or quantification of target proteins as well.

In particular, the method of the invention is based on amperometric detection of target nucleic acids or polypeptides by forming complex target nucleic acids or polypeptide/enzyme/polymeric activator bilayers, carried out preferably on a sensor array.

According to a first aspect, the invention provides a method for the detection and/or quantification of at least one target nucleic acid or target polypeptide in a sample of nucleic acids or polypeptides comprising the steps:
a) providing a sample comprising nucleic acids or polypeptides;
b) labelling the nucleic acids or polypeptides with a ligand conjugate, the ligand conjugate comprising a first element binding to the nucleic acids or polypeptides and a second element which is a capture ligand;
c) contacting the nucleic acid-ligand conjugates or polypeptide-ligand conjugates with at least one capture probe, the capture probe hybridising with or binding to at least one target nucleic acid or target polypeptide;
d) adding i) an oxidoreductase enzyme, wherein the oxidoreductase enzyme is recognised by the capture ligand, or ii) a complex comprising an oxidoreductase enzyme bound to a capture receptor, the capture receptor capable of binding to the capture ligand;
e) adding a redox polymer, the redox polymer binding to the oxidoreductase enzyme, thereby resulting in the transfer of electrons from the enzyme via the redox polymer to an electrode surface; and
f) detecting and/or quantifying the presence of the target nucleic acid(s) or target polypeptide(s).

The capture probe may be fixed onto an electrode surface. Alternatively, the capture probe may be free in solution and comprise means to be able to fix to an electrode surface. The means for fixing to an electrode surface may be any means which allows the selection and recovery of the capture probe bound to the target nucleic acids or polypeptides and allow the capture probe to be fixed on the electrode substrate. For example, an antibody may be used.

Alternatively, the means could consist the use of magnetic beads, which allow the selection and recovery of the capture probe bound to the target nucleic acids or polypeptides and allow the capture probe to be bound or fixed to an electrode surface capable of attracting the magnetic beads. According to these alternatives, only the nucleic acids or polypeptides (the targets) bound to the capture probe are selected and fixed onto the electrode surface.

The sample of nucleic acids can be a sample of mRNAs, cDNAs and/or genomic DNA. A sample of cDNA is for example a cDNA library, from which the desired target cDNA(s) is selected. When the sample is a sample of genomic DNA or total mRNA, the sample may be any biological sample, for example obtained from a tissue. The sample or tissue may be obtained from a mammal. Therefore, it could be, for example, a human or mouse sample or tissue.

When the sample is a sample of nucleic acids, like mRNAs, cDNAs and/or genomic DNA, the capture probe is an oligonucleotide complementary to and capable of hybridising with at least one portion of the target nucleic acid(s).

According to a particular embodiment, the sample is a sample of total mRNA, and the capture probe fixed on the electrode surface is an oligonucleotide complementary to a portion of the target mRNA(s).

Accordingly, this method is indicated as the direct detection and/or quantification mRNA method.

For the purposes of the present invention, a nucleic acid molecule, for example an oligonucleotide, is "hybridisable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridisation and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly in Chapter 11 and Table 12.1 therein (entirely incorporated herein by reference). The conditions of temperature and ionic strength determine the "stringency" of the hybridisation. Hybridisation requires the two nucleic acids to contain complementary sequences, although depending on the stringency of the hybridisation, mismatches between bases are possible. The appropriate stringency for hybridising nucleic acids depends on the length of the nucleic acids and the degree of complementation, variables well known in the art. The greater the degree of similarity or homology between the two nucleotide sequences, the greater the value of Tm for hybrids of nucleic acids having those sequences. The relative stability (corresponding to higher Tm) of nucleic acid hybridisations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridisations with shorter nucleic acids, i.e., oligonucleotides, the position of mismatches becomes more important, and the length of the oligonucleotide determines its specificity (see Sambrook et al., supra, 11.7-11.8). Furthermore, the skilled artisan will recognize that the temperature and wash solution salt concentration may be adjusted as necessary according to factors such as the length of the probe. The term "complementary" is used to describe the relationship between nucleotide bases that are capable of hybridising to one another. For example, with respect to DNA, adenosine is complementary to thymine and cytosine is complementary to guanine.

When the sample is a sample of polypeptides, for example proteins, the capture probe may be any ligand capable of recognising and binding to the target polypeptide, for example an antibody specific to the target polypeptide.

With reference to the ligand conjugate, the first element binding to the nucleic acids or to the polypeptides may be cisplatin (Hoevel T., et al., Biotechniques, 27(5):1064-7, 1999), platinum-linked Cyanine 3 and/or platinum-linked Cyanine 5 (Gupta et al., Nucleic Acids research, Vol. 31, No. 4, 2003). Other elements that bind to the nucleic acids include suitable proteins that have an affinity to or bind to DNA, like single stranded binding proteins (SSB), recA or its homologues, mismatch detecting proteins of bacterial, viral or mammalian origin, or other proteins that associate with DNA.

The capture ligand may be any a liable (exchangeable) ligand capable of binding to the capture receptor, like biotin, digoxigenin, an antibody or antigen binding to the capture receptor, an antibody binding to the oxidoreductase enzyme, an aptamer, a protein and/or a protein receptor.

The capture receptor may be avidin, streptoavidin, anti-digoxigenin, an antigen or antibody binding to the capture ligand, an aptamer, a protein and/or a protein receptor.

According to a particular embodiment, the ligand conjugate is cisplatin coupled to digoxigenin derivative (Hoevel T., et al., Biotechniques, 27(5):1064-7, 1999), or cisplatin-biotin and the capture receptor is avidin or streptoavidin (both alternatives herein also indicated as "strept(avidin)").

According to another embodiment, it provides a complex comprising an oxidoreductase enzyme bound to strep(avidin). For example, GOX-strep(avidin).

According to another embodiment, oxidoreductase enzyme is added by itself (therefore not in the form of a complex with the capture receptor) and the oxidoreductase enzyme is capable of binding to the capture ligand. In this case, the capture ligand may be an antibody recognising and binding to the oxidoreductase enzyme.

The oxidoreductase enzyme may be any enzyme suitable for the purposes of the present invention, for example an oxidase, a dehydrogenase, a mono-oxygenase, a hydroxylase, a dioxygenase, a peroxidase, a hydrogenase, or the like. The oxidase, may be any oxidase suitable for the purposes of the present invention, for example, glucose oxidase (GOX or GOx), lactase oxidase (LAX), pyruvate oxidase (PYX), tyrosinase, horseradish peroxidase (HRP), ascorbic acid oxidase, laccase, belirubin oxidase, or a mixture thereof.

The redox polymer may be any redox polymer known in the art and suitable for the purposes of the present invention. For example, the redox polymer may be a redox active polymeric material, poly(vinylimidazole-co-acrylamide), poly(vinylimidazole-co-acrylamide) partially imidazole-complexed with [Os(bpy)$_2$], [Os(dmbpy)$_2$], [(Osbpy)$_2$(im), [Os(dabpy)$_2$] and/or [Os(bpy)$_2$(Mim)], poly[vinylpyridine Os(bis-bipyridine)$_2$Cl-co-allylamine] (PVP-Os-M), horseradish peroxidase (HRP), ferrocene-based polymer, and/or ruthenium-based polymers.

According to a particular embodiment, the method of the invention is a diagnostic method for the detection and/or quantification of one or more target genes. The target gene may comprise of at least one of the following: tumor protein p53 (TP53), heat-shock protein 90 (HSP90), breast cancer gene 1 (BRCA1), and/or Histone H4 (His4). The diagnostic method according to the invention may also detect and/or quantify different target genes at the same time. Further, suitable markers may be used.

The method according to the invention allows for the detection of very small amounts of nucleic acids or polypeptides. For example, when the sample is a sample of total mRNA, the method of the invention allows for the detection of target mRNA(s) within the limits of 0.20-1.0 fg (femtograms), in particular, of 0.10-0.95 fg.

Figure 2:
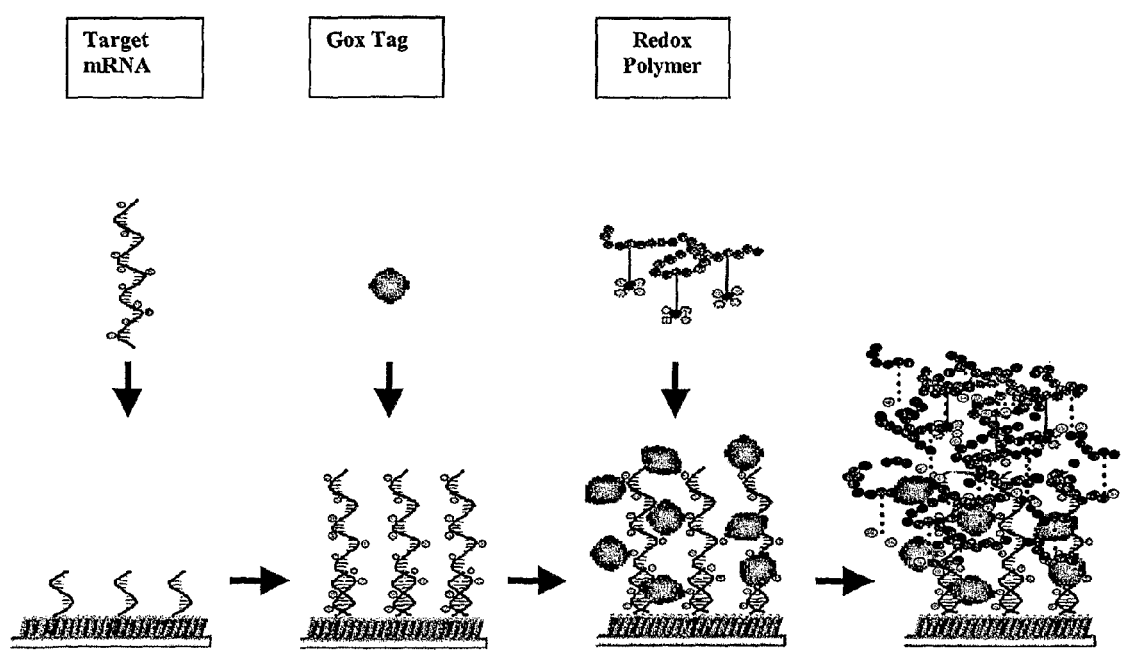
FIG. 2 Schematic illustration of RNA assay using the RNA/redox polymer bilayer model.

According to a particular embodiment, the invention provides a method which is exemplified in FIG. 2. The method represents a novel approach that allows the direct detection of specific genes in total mRNA extracted from human breast tissues. The mRNA is labeled in a single-step non-enzymatic reaction using the cisplatin-biotin conjugate. After hybridization with complementary oligonucleotides immobilized on a gold electrode surface, formation of a nucleic acid/polymeric activator bilayer allows for the sensitive amperometric detection. The detection limit of the system for target mRNA is at femtomolar levels. It translates to 0.20-1.0 fg of mRNA. In practice, this level of biosensor sensitivity meets the requirements for a direct detection of mRNA in real-world samples without the need for a PCR step. Multiple assays were successfully attempted on a sensor array, for example on a 8×8 sensor array.

The sensitivity of the method of the invention was greatly improved, compared to the methods known in the art, by as much as 40-fold by incorporating multiple enzyme labels to the mRNA molecules. As low as 0.80-fold difference in TP53 gene expression was successfully detected in the total mRNA. With the greatly improved sensitivity, at least 1000-fold more sensitive than fluorescence-based techniques, the amounts of total mRNA needed in the assay were cut down from microgram to nanogram levels. This system provides an ultrasensitive method for the direct mapping of breast cancer genes and constitutes a complete system for molecular diagnosis.

According to another aspect, the present invention provides a device for carrying out the method of the invention. An example of the device according to the present invention is exemplified in FIG. 1(A,B). The example shown in FIG. 1(A,B) is not a limiting example of the device according to the invention.

The device consists of a sensor array. In particular, a sensor array device for the detection of target nucleic acids and/or polypeptides in a sample analyte comprising a first and second electrode separated by a spacer/insulating layer, and wherein the electrode become connected when the analyte is applied to the second electrode. The current passing through the two electrodes reflects the quantity of analyte applied. The electrode material is made of any material suitable for the purposes of the present invention. For example, the electrode material may be made of gold, platinum, glassy carbon, graphite, carbon pastes (CPE), carbon-epoxy composites for amperometry, doped diamond film, carbon nanotubes, Indium-Tin oxide, and/or any conductive materials, such as conductive polymer, doped semiconductors. In particular, the spacer/insulator layer comprises from the bottom to the top, an adhesive spacing/insulating layer, optionally a screen-printed layer and a hydrophobic layer. The screen-printed layer may be a Ag/AgCl. Further, the first electrode may be applied on a support. The support may be any suitable support for the purposes of the present invention, for example, a glass support. The capture probe may be applied on the surface of the first electrode. The capture probe is capable of hybridising with or binding to at least one target nucleic acid or target polypeptide of the analyte. The analyte may be a sample of total mRNA, a sample of cDNAs or genomic DNAs.

The sensor array works as follows. There are two layers of electrodes separated by an insolating layer. Before applying solution they are disconnected, and will become connected when a drop of solution is applied, the current passing through the two electrodes reflects the quantity of analyte in that drop. Detection of individual genes in the total mRNA (or any other nucleic acids or polypeptides) was performed on the sensor array. The individual sensors remain open-circuit, for example until a 10 μl aliquot of 40 mM glucose test solution is applied. Withdrawal of the test solution effectively disables the sensor. Amperometric measurements are carried out at the suitable Voltage. For example, as shown in the experimental part, they were carried out at 0.36 V. All potentials reported in this work were referred to the Ag/AgCl reference electrode, however, the reference electrode is not limited to this chemical composition.

Recent advances in μ-fluidics and microelectromechanical systems (MEMS), Micro Total Analytical Systems (μTAS) and biochip technology have led to the miniaturization of many micro-scale analytical instruments. The advantages of miniaturization in fluid processing include improved efficiency with regards to sample size, response times, cost, analytical performance, process control, integration, throughput and automation (de Mello, Anal. Bioanal. Chem. 372: 12-13, 2002). According to a particular aspect, the device according to the invention is integrated in a microelectromedical system (MEMS) and/or fully automated Micro Total Analysis System (μ-TAS).

According to another aspect, the invention provides a diagnostic kit comprising the following components: A) at least one capture probe i) fixed on an electrode surface, or ii) comprises means that enables it to fix to an electrode surface; B) a ligand conjugate for labelling nucleic acids or polypeptides of a sample, the ligand conjugate comprising a first element binding to the nucleic acids or polypeptides and a second element which is a capture ligand; C) i) an oxidoreductase enzyme, wherein the oxidoreductase enzyme is capable of being bound by the capture ligand, or ii) a complex comprising an oxidoreductase enzyme bound to a capture receptor, the capture receptor capable of binding to the capture ligand; D) a redox polymer.

Having now generally described the invention, the same will be more readily understood through reference to the following examples, which are provided by way of illustration and are not intended to be limiting of the present invention.

EXAMPLES

Materials

Unless otherwise stated, reagents were obtained from Sigma-Aldrich (St Louis, Mo., USA) and used without further purification. Glucose oxidase-avidin conjugates (GOx-A) were purchased from Vector Laboratories (San Diego, Calif., USA). Cisplatin-coupled biotin conjugates (Biotin-Chem-Link) were obtained from Roche Diagnostics (Mannheim, Germany). [Osmium(2,2'-bipyridine)$_2$Cl$_2$]Cl ([Os(bpy)$_2$]), [Osmium(4,4'-dimethyl-2,2'-bipyridine)$_2$Cl$_2$]Cl, ([Os(dmbpy)$_2$]) and [Osmium(4,4'diamino-2,2'-bipyridine)$_2$Cl$_2$]Cl ([Os(dabpy)$_2$]) were synthesized from K$_2$OsCl$_6$ following the proposed procedure by Lay et al. (Lay, P. A., et al., Inorg. Synth. 24, 291, 1986, herein incorporated by reference). [Osmium(2,2'-bipyridine)$_2$(1-methylimidazole)Cl]Cl$_2$ ([Os(bpy)$_2$(Mim)]) and [Osmium(2,2'-bipyridine)$_2$(imidazole)Cl]Cl$_2$ ([(Os(bpy)$_2$(im)]) complexes were prepared from the [Os(bpy)$_2$Cl$_2$] complex according to literature procedures (Sullivan, B. P., Salmon D. & Meyer, T. J. Inorg. Chem., 1978, 17, 3334, herein incorporated by reference). The redox polymers used in this study were poly(vinylimidazole-co-acrylamide) partially imidazole-complexed with [Os(bpy)$_2$] (I), [Os(dmbpy)$_2$] (II), [(Os(bpy)$_2$(im)] (III), [Os(dabpy)$_2$] (IV) and [Os(bpy)$_2$(Mim)] (V). Synthesis of these redox polymers was described elsewhere (Gao, Z., Binyamin, G., Kim, H. H., Barton, S. C., Zhang, Y. & Heller, A. Angew. Chem. Int. Ed. 2002, 41, 810, herein incorporated by reference). A phosphate buffered-saline (PBS, pH 7.4) was used for washing and electrochemical measurements. All oligonucleotides were custom-made by AlphaDNA (Montreal, Canada).

Total mRNA Extraction and Labeling

Total mRNA in human breast tissues was extracted with a Dynabeads® mRNA DIRECT™ Kit (Dynal ASA, Oslo, Norway) according to the manufacturer's recommended protocol. The total mRNA was directly labeled using the cisplatin-coupled biotin conjugates, according to the recommended procedure by Roche Diagnostics. As shown in Scheme 1, this conjugate consists of a biotin moiety, which is bound by an aliphatic linker to a cisplatin complex. One binding site is covalently bound to the linker/biotin molecule, and the other site is a cleavable nitrate ligand. Incubation in an aqueous solution with nucleic acid templates (DNA or RNA) cleaves the nitrate and a new complex is formed between cisplatin and the N$_7$ position of G and A bases. The coordinative compound is stable and resistant to nucleic acid denaturation. Typically, 1.0 μg of total mRNA was used in each of the labeling reactions. In our experiments, 1.0 μl of cisplatin-biotin conjugate was incubated at 85° C. for 30 min with 1.0 μg of total mRNA at a final volume of 20 μl, and the reaction was terminated by the addition of 5 μl of stop solution. The final product was stored at −20° C.

Scheme 1: Structure of cisplatin-biotin conjugate (Biotin-Chem-Link).

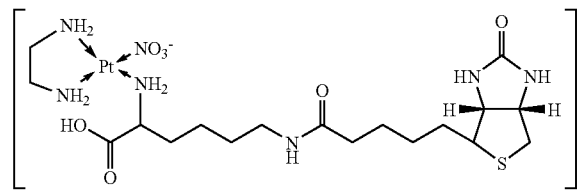

Nucleic Acid Sensor Array Fabrication

A titanium adhesion layer of 25-50 Å was electron-beam evaporated onto a glass slide followed by 2500-3000 Å of gold. A patterned spacer/insulator layer, consisting of a patterned 1-mm thick adhesive spacing/insulating layer with a screen-printed Ag/AgCl layer and a hydrophobic layer were assembled, as shown in FIG. 1(A,B). The diameter of the individual sensor (which is represented in FIG. 1(A,B) by the dots in the top view) was 2.0 mm and that of the top hydrophobic pattern was 4 mm. 2.5 μl aliquots of 50 μM capture probe solutions were applied to the plasma cleaned individual sensors by carefully placing the solutions on the sensor surfaces and incubating for at least 12 hours in a controlled environment. After washing off unbound probes, 2.5 μl aliquots of 50 μM 1-mercaptododecane (MD) in ethanol were applied for 4-6 hours to block uncovered gold. The sensor array was ready after thoroughly rinsing with water. The sensor array works as follows. There are two layers of electrodes separated by an insolating layer. Before applying solution they are disconnected, and will become connected when a drop of solution is applied, the current passing through the two electrodes reflects the quantity of analyte in that drop. Detection of individual genes in the total mRNA was performed on the sensor array. The individual sensors remain open-circuit until a 10 μl aliquot of 40 mM glucose test solution is applied. Withdrawal of the test solution effectively disables the sensor. Amperometric measurements were carried out at 0.36 V. All potentials reported in this work were referred to the Ag/AgCl reference electrode.

Hybridization and Enzyme Labeling

Breast cancer susceptibility genes, namely, tumor protein p53 (TP53, 1182 bp), heat-shock protein 90 (HSP90, 1632 bp), breast cancer gene 1 (BRCA1, 5592 bp), and Histone H4 (His4, 312 bp) in the total mRNA extract were selected and used as explained later. A house-keeping gene, glyceraldehyde-3-phosphate dehydrogenase (GAPDH, 1008 bp), was also tested to further verify the system. cDNAs transcribed from the mRNAs of the corresponding genes extracted from the human breast tissues were used as analyzed nucleic acids in a calibration study. A 10 mM Tris-HCl-1.0 mM EDTA-0.10 M NaCl buffer solution (TE) was used as the hybridization buffer. Hybridization was carried out in a 55° C. water bath for 30 min. Nucleic acid samples were denatured at 95° C. (cDNA) and 70° C. (mRNA) for 10 min and cooled in an ice bath before being added to the sensor array. After hybridization, the sensor array was exposed to 2.5 µl aliquots of 5.0 mg/ml GOx-A at room temperature for 30 min and soaked for 5 min in a stirred PBS solution, a procedure aimed at removing any non-DNA related GOx-A uptake. To ensure the maximal loading of the redox polymer, the electrode was then exposed for at least 10 min to 2.5 µl aliquots of 5.0 mg/ml redox polymer solution and thoroughly rinsed with PBS thereafter.

Electrochemical Measurement

Electrochemical measurements were carried out in a Faraday cage with a low-noise CH Instruments Model 660A electrochemical workstation equipped with a low-current module in conjunction with a Pentium computer. Cyclic voltammetry was conducted in both PBS buffer and PBS buffer containing 40 mM glucose. Electrochemical characterization was carried out with a gold electrode. An Ag/AgCl electrode was used as the reference electrode and a platinum wire as the counter electrode. Detection of individual genes in the total mRNA was performed on the sensor array. The individual sensors remain open-circuit until a 10 µl aliquot of 40 mM glucose test solution was applied. Withdrawal of the test solution effectively disabled the sensor. Amperometric measurements were carried out at 0.36 V. All potentials reported in this work were referred to the Ag/AgCl reference electrode.

Detection Scheme

The scheme for detecting mRNA through direct hybridization and formation of the mRNA+GOxA/redox polymer bilayer is shown in FIG. 2. Prior to the test, mixtures of thiolated oligonucleotide capture probes and thiol molecules were immobilized onto the sensor array surfaces through self-assembly. The sensor array was then exposed to the target gene solutions. Following hybridizations to their complementary biotinylated target mRNAs, GOx-A labels were introduced to the system via an avidin-biotin interaction. A redox polymer overcoating was then brought to the sensor array through layer-by-layer electrostatic self-assembly. The redox polymer layer acts as a mediating layer for the enzymatic reaction. It electrochemically activates the enzyme labels, attached to the target genes. In the presence of substrate molecules, the current generated from enzymatic oxidation of the substrate was detected amperometrically and it correlates directly to the target mRNA concentration in the sample solution.

Synthesis of Cisplatin-biotin Conjugate Labeled mRNA

Figure 3:
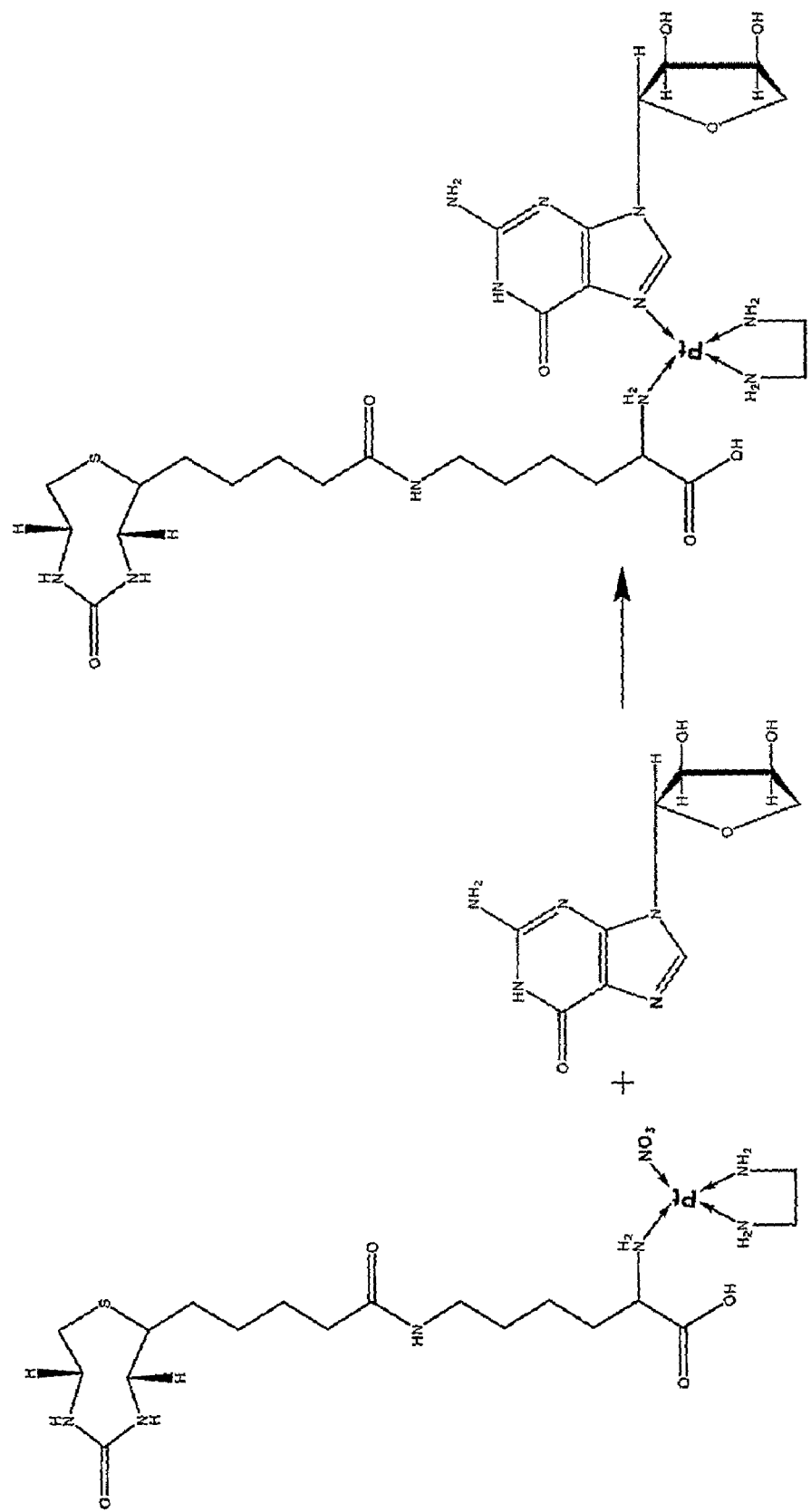
FIG. 3 Cisplatin labelling mechanism.
Figure 4:
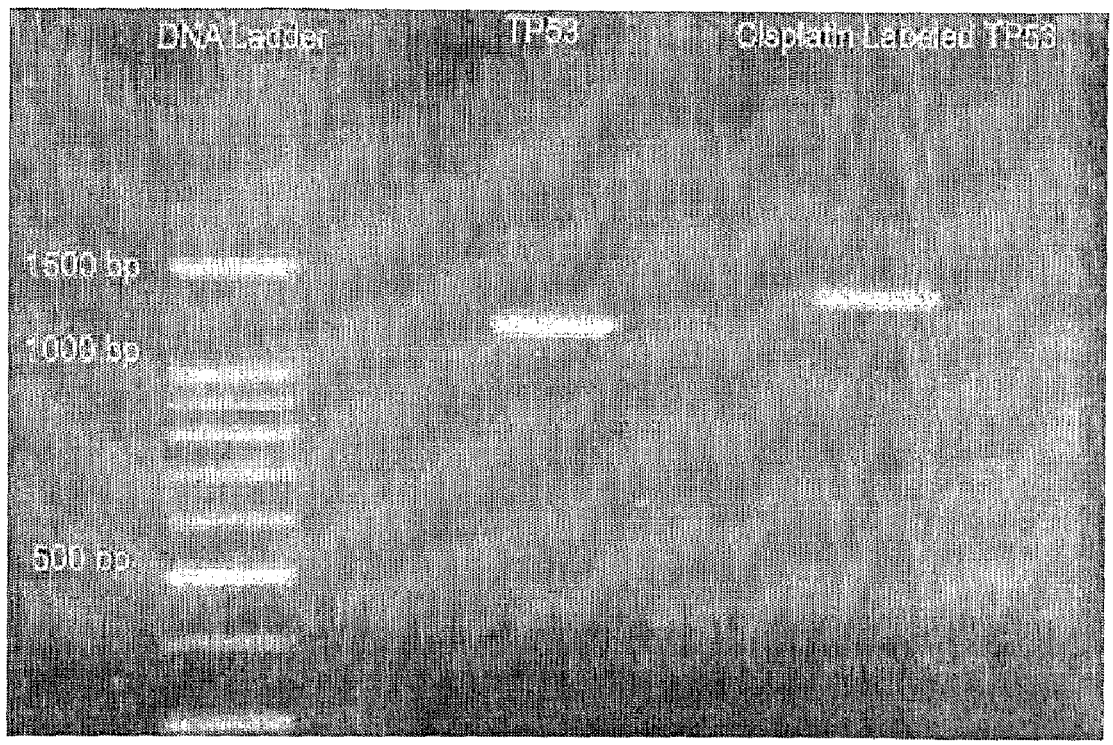
FIG. 4 Agarose gel electrophoretic results of cisplatin-biotin conjugates labeled TP53. The samples were run at 10 V/cm in 0.090 M Tris-0.090 M boric acid—0.0020M EDTA buffer on a 2.5% agarose gel.

Instead of labeling the nucleic acid using biotin tagged nucleotides during a RT-PCR process, incubation of the nucleic acid templates with the cisplatin-biotin conjugates also leads to satisfactory labeling (FIG. 3). As illustrated in FIG. 4, taking TP53 as an example, full length TP53 mRNA retained its integrity after reaction with cisplatin-biotin conjugates. Compared to non-labeled TP53 (lane 2), the lower mobility shift of the reaction product (lane 3) suggests successful incorporation of cisplatin-biotin conjugates to the mRNA chain. Quantitative analysis showed that 8-10% of the bases in TP53 mRNA were successfully labeled (Hoevel, T., Holz, H. & Kubbies, M. Biotechniques 1999, 27, 1064). This labeling efficiency was sufficient for subsequent GOx-A loading. The experiments indicated that it was not possible to attach GOx-A to every cisplatin-biotin moiety on the mRNA molecule. On average, one GOx-A conjugate was attached to the mRNA molecule per 40-45 bases, or ~30% of biotin moieties. To attain the highest sensitivity and best reproducibility, both cisplatin-biotin and GOx-A labeling processes were optimized to ensure maximal loading of the biotin and GOx-A labels. Similarly, multiple biotin moieties were also incorporated into all other mRNA molecules upon incubation of the total mRNA with cisplatin-biotin conjugates at 85° C. for 30 min.

Hybridization and Feasibility Study of Target Gene Detection

Figure 5:
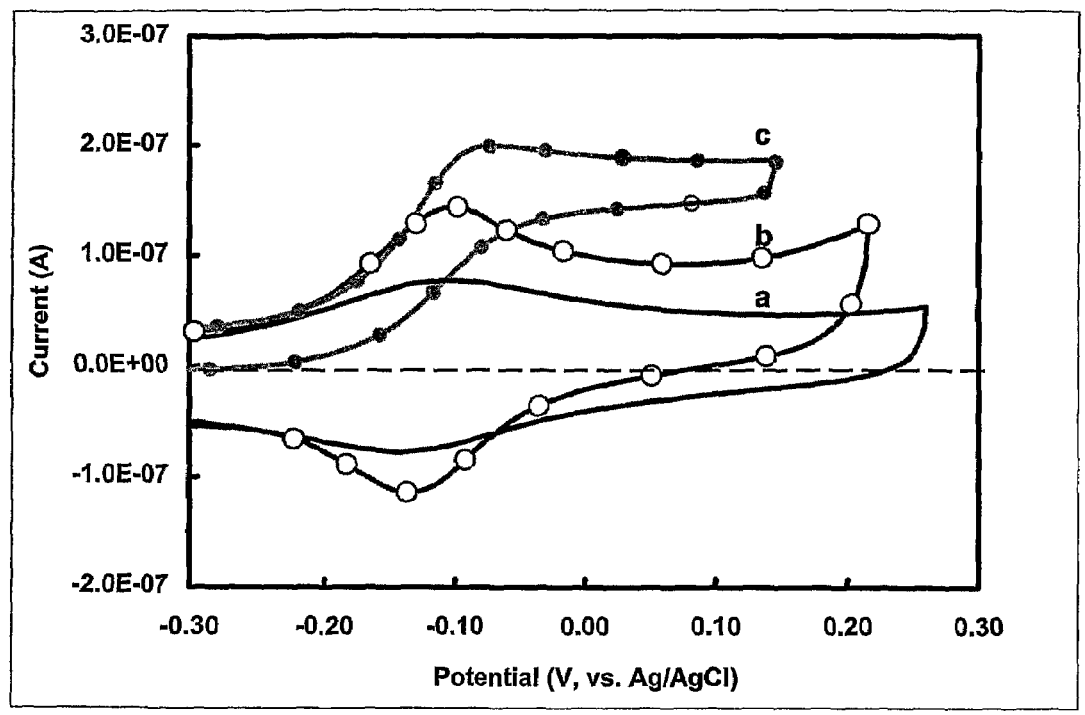
FIG. 5 Cyclic voltammograms of sensors at 25 mV/s in PBS (a) before and (b) after hybridization with TP53 in 500 ng total mRNA, incubation with GOX-A; and (c) after adding 40 mM glucose to the PBS. VI overcoatings were applied to all sensors. Conditions are detailed in the Experimental Section.

The formation of the mixed self-assembled monolayer on the sensor array was routinely monitored by surface coverage and electrochemical measurements. All the data obtained indicated a single compact mixed molecular layer, comprising oligonucleotide capture probes and space-filling 1-mercaptododecane molecules on the sensor surface. Since the redox polymer used in this work was positively charged and the sensor surface was negatively charged, a brief soaking of the sensor in the 5.0 mg/ml redox polymer solution, resulted in the formation of a nucleic acid/redox polymer bilayer on the electrode via the layer-by-layer electrostatic self-assembly (Decker, G. Science 1997, 277, 1231). As illustrated in FIG. 5 curve 'a', the brayer coated sensor behaved as expected for a highly reversible surface immobilized redox couple with little change after exhaustive washing and after numerous repetitive potential cycling between −0.30 and +0.60 V, revealing a highly stable surface confined electrostatic bilayer (Bard, A. J. & Faulkner, L. R. Electrochemical Methods. John Wiley & Sons: New York, 2001, p 590). Such results ascertained that all of the osmium redox centers were allowed to reach the electrode surface and proceed to reversible heterogeneous electron transfer. The total amount of bound osmium redox centers, depending on the amount of anionic species (capture probes), $1.5$-$2.5\times10^{-10}$ mole/cm$^2$, was estimated from the area under either the oxidation or the reduction current peak corrected from the background current. Subsequent voltammetric tests in the ferricyamide solution showed a voltammogramidentical to that obtained at a bare gold electrode. These changes were attributed to the decrease in the electron tunneling pathway due to the formation of the bilayer which brought the osmium redox centers to the closest possible proximity with the electrode surface, and more importantly, the fast electron transfer rate of the osmium redox centers in the bilayer which minimized the effect of electron tunneling across the underlying insulating monolayer and mediated electron transfer from solution species to the electrode surface (Xie, H.; Yu, Y. H.; Mao, P: L.; Gao, Z. Nucleic Acids Res. 2004). As shown later, the presence of nucleic acids and GOx-A in the film did not appreciably alter the electrochemistry of the redox polymer.

In a first hybridization test, full length TP53 mRNA in the total mRNA was selected as the target gene. Prior to the hybridization, the mRNA mixture was denatured at 70° C. for 10 min. All primers used for RT-PCR were custom-made by 1st BASE (Singapore). The primer sequences were as follows: GAPDH sense, 5'-ATGGTGMGGTCGGTGTCM-3' (SEQ ID NO: 1); GAPDH antisense, 5'-TTACTCCTTG-GAGGCCATGT-3' (SEQ ID NO:2); TP53 sense, 5'-ATG-GAGGATTCACAGTCGGA-3' (SEQ ID NO:3); and TP53 antisense, 5'-TCAGTCTGAGTCAGGCCC-3' (SE Q ID NO:4).

TABLE 1

Oligonucleotide capture probes used in the study

Detection of TP53 gene

Capture probes
5'-HS-$(CH_3)_6$-$(A)_{12}$-ATGGAGGATTCACAGTCG GA-3' (SEQ ID NO:5)
5'-HS-$(CH_3)_6$-$(A)_{12}$-TCAGTCTGAGTCAGGCCC CA-3' (SEQ ID NO:6)

Detection of GAPDH gene

Capture probes
5'-HS-$(CH_3)_6$-$(A)_{12}$-TTACTCCTTGGAGGCCAT GTAGG-3' (SEQ ID NO:7)
5'-HS-$(CH_3)_6$-$(A)_{12}$-ATGGTGAAGGTCGGTGTC AACGG-3' (SEQ ID NO:8)

Control experiment

Capture probe
5'-HS-$(CH_3)_6$-$(A)_{12}$-CCTCTCGCGAGTCAACAG AAACG-3' (SEQ ID NO:9)

Oligonucleotides with sequences complementary to the TP53 gene were immobilized on the sensor surface and served as capture probes. Upon hybridization at 55° C. for 30 min, TP53 mRNA from the mixture was selectively bound to its complementary capture probes and became fixed on the sensor surface. Thorough rinsing with the hybridization buffer washed off all of the non-hybridization related mRNA. GOx-A labels were brought to the sensor surface via biotin-avidin interaction during a subsequent incubation with Gox-A conjugates. A typical cyclic voltammogram of the sensor after applying the redox polymer overcoating is shown in FIG. 5, curve 'b'. As seen in curve 'b', considerably higher peak currents were observed for both oxidation and reduction processes at the TP53 mRNA treated sensor, indicating that an increased amount of redox polymer was brought to the sensor surface, most probably due to the captured mRNA molecules which brought more negative charges to the sensor surface and created a micro three-dimensional structure on the sensor. Treating the sensor in the redox polymer solution resulted in the formation of a mixed micro three-dimensional mRNA+GOx-A/redox polymer bilayer. The total amount of redox polymer, $5.9$-$8.6 \times 10^{-10}$ mole/$cm^2$, was considerably higher than that of a redox polymer monolayer, $\sim 10^{-11}$ mole/$cm^2$, suggesting that the redox polymer chains were densely 'grafted' on the electrode in the three-dimensional network configuration. This bilayer also had very rapid electron-exchange processes: At scan rates of up to 500 mV/s, the separation of the current peaks of the voltammetric electroreduction and electrooxidation waves was generally less than 25 mV for the bilayer containing GOx-A labels. Extensive washing and potential cycling produced no noticeable changes, indicating that the redox polymer was robustly bound at the sensor surface through the formation of the electrostatic bilayer and to some degree, interaction with the first nucleic acid layer. FIG. 5, curve 'c', was the voltammogram in PBS containing 40 mM glucose after hybridization. An obvious catalytic current was observed due to the presence of glucose oxidase in the bilayer. In a control experiment, non-complementary capture probe failed to capture any TP53 and thereby no enzyme labels were able to bind to the sensor surface. No noticeable catalytic current in voltammetry was obtained.

Figure 6:
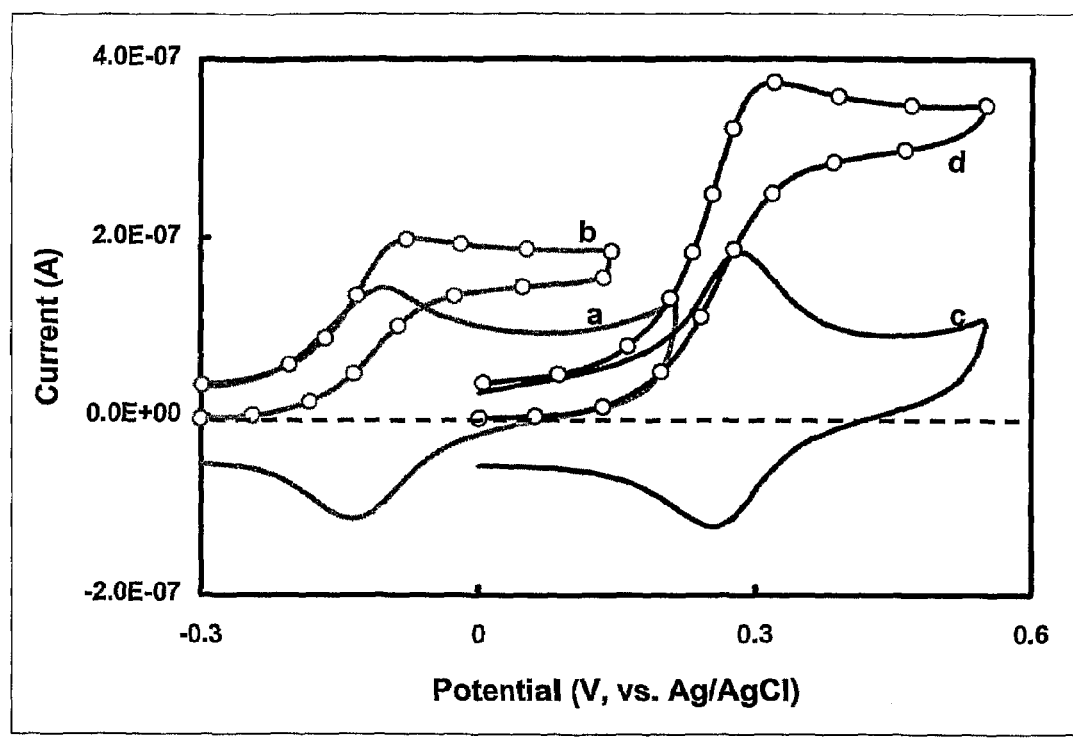
FIG. 6 Cyclic voltammograms of sensors at 25 mV/s in PBS after hybridization in with TP53 in 500 ng total mRNA, incubation with GOX-A and applying redox polymer overcoating (a and c); and (b and d) after adding 40 mM glucose to the PBS. IV overcoatings were applied to (a) and (b); and III overcoatings were applied to (c) and (d). Conditions are detailed in the Experimental Section.

As can be seen in FIG. 6 and Table 2, structural differences in the redox polymer overcoating strongly affected its mediating capability.

TABLE 2

Electrochemical characteristics of electrode with different redox polymer overcoating

| Redox Polymer | $E_m$ (mV) | $\Delta E_p$ (mV) | Polymer Loading ($\times 10^{10}$ mole/$cm^2$) | $i_{cat}$ (nA) |
|---|---|---|---|---|
| I | 112 | 19 | 6.6 | 138 |
| II | 20 | 22 | 5.9 | 110 |
| III | 285 | 20 | 7.8 | 240 |
| IV | −114 | 28 | 6.3 | 82 |
| V | 293 | 18 | 8.6 | 186 |

$E_m = \frac{1}{2}(E_{pa}+E_{pc})$, $\Delta E_p = E_{pa} - E_{pc}$

The polymers (I), (II), (III), (IV) and (V) refer to those described in the section "Materials".

The catalytic currents of redox polymers in which the osmium redox centers bearing two positive charges were higher than those with a single positive charge implied that electrostatic interaction of GOx-A and the osmium redox center was one of the important factors in a successful mediation, as the isoelectrical point of GOx was around 4.0 (Trudeau, F., Daigle, F. & Leech, *D. Anal. Chem.* 1997, 69, 882). Acrylamide moieties in the redox polymer also helped to stabilize the bilayer and bring the osmium redox centers to close proximity of GOx. It was observed that the catalytic currents generated with the redox polymer containing 1-substituted imidazole ligand was smaller than that containing non-substituted imidazole, suggesting that hydrogen bonding between imino groups and carboxyl groups on GOx in the vicinity of the FAD redox centers of GOx further facilitated electron exchange. Under identical experimental conditions, the voltammetric catalytic current generated at the sensor employing a III overcoating (the redox polymer III) was the highest and was measured to be 3-fold higher than that observed at the sensor with a IV overcoating (the redox polymer IV). Therefore, to attain the highest current sensitivity, III was used in subsequent experiments.

Figure 7:
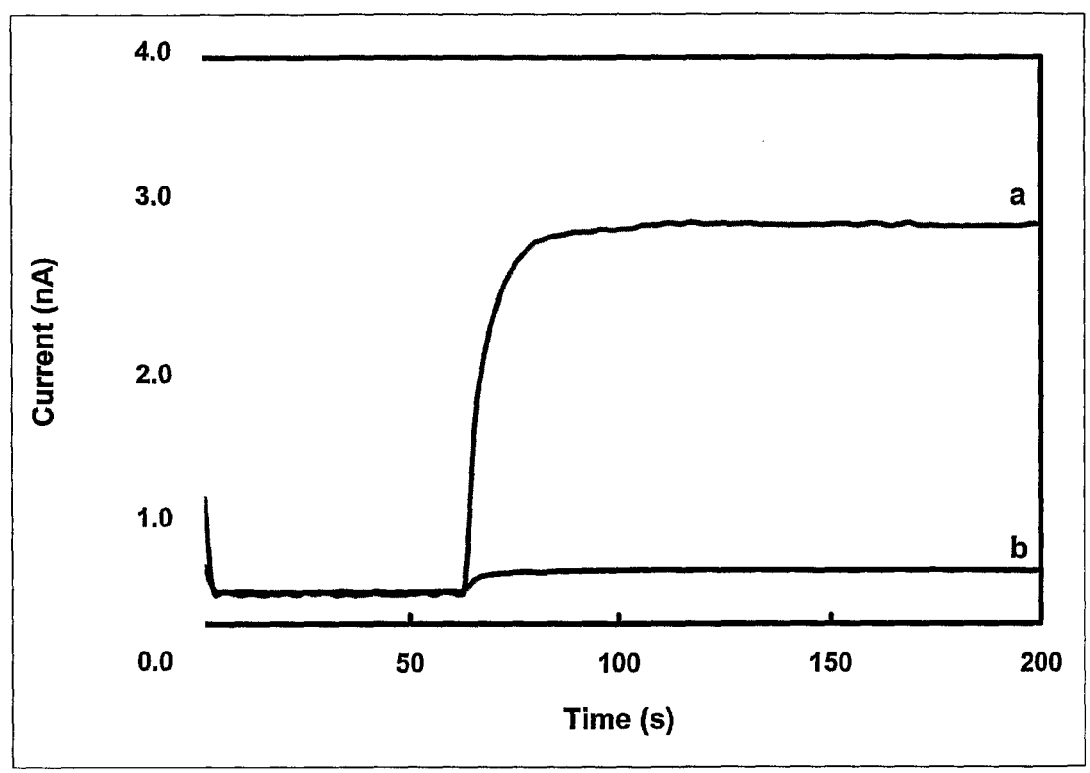
FIG. 7 Amperometric responses of sensors after hybridization with TP53 in 20 ng total mRNA (a) with complementary and (b) non-complementary capture probes, incubation with GOX-A and applying III overcoatings. Poised potential: 0.36 V, 40 mM glucose. Conditions are detailed in the Experimental Section.

In another test, after hybridization with TP53 in 20 ng total mRNA, the completed sensor was immersed in the PBS buffer solution. The oxidation current in amperometry increased by 2.7 nA at 0.36 V (vs. Ag/AgCl) upon addition of 40 mM glucose to the PBS solution (FIG. 5, curve a). In a control experiment where non-complementary capture probes were immobilized on the sensor surface, only a 0.18 nA increment was observed (FIG. 7, curve 'b'). The amperometric results agreed well with the cyclic voltammograms obtained earlier and confirmed again that TP53 was successfully detected from the total mRNA mixture with high specificity, considering that there were tens of thousands of genes in the total mRNA. In a similar way, by changing capture probes immobilized on the sensor surface, all other genes were also successfully detected from the total mRNA.

Detection of Target Gene with a Single Base Mismatch

Figure 8:
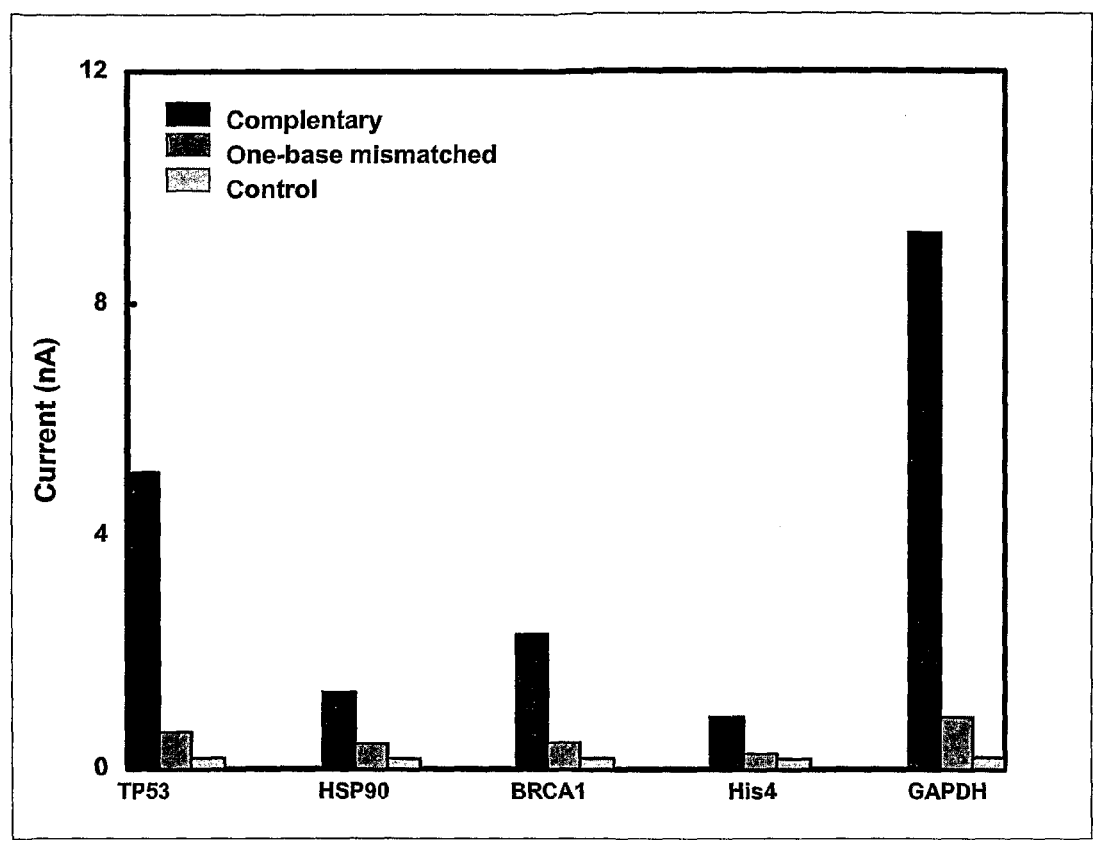
FIG. 8 Amperometric responses of sensors after hybridization in the mRNA mixture with capture probes complementary, one-base mismatch and non-complementary to the genes in 40 ng total mRNA. Conditions are the same as for FIG. 7.

The specificity of the assay for detection of target genes was further evaluated in 40 ng of total mRNA by replacing fully complementary capture probes with probes in which one of the bases was mismatched. As shown in FIG. 8, the current increments for the perfectly matched sequence were in the range of 0.80-9.2 nA, whereas, for one base mismatch, the increments dropped by 80% to as low as 0.23 nA, slightly higher than 0.19 nA observed for non-complementary sequence (control sensor).

Calibration Curves for Target Genes

Figure 9:
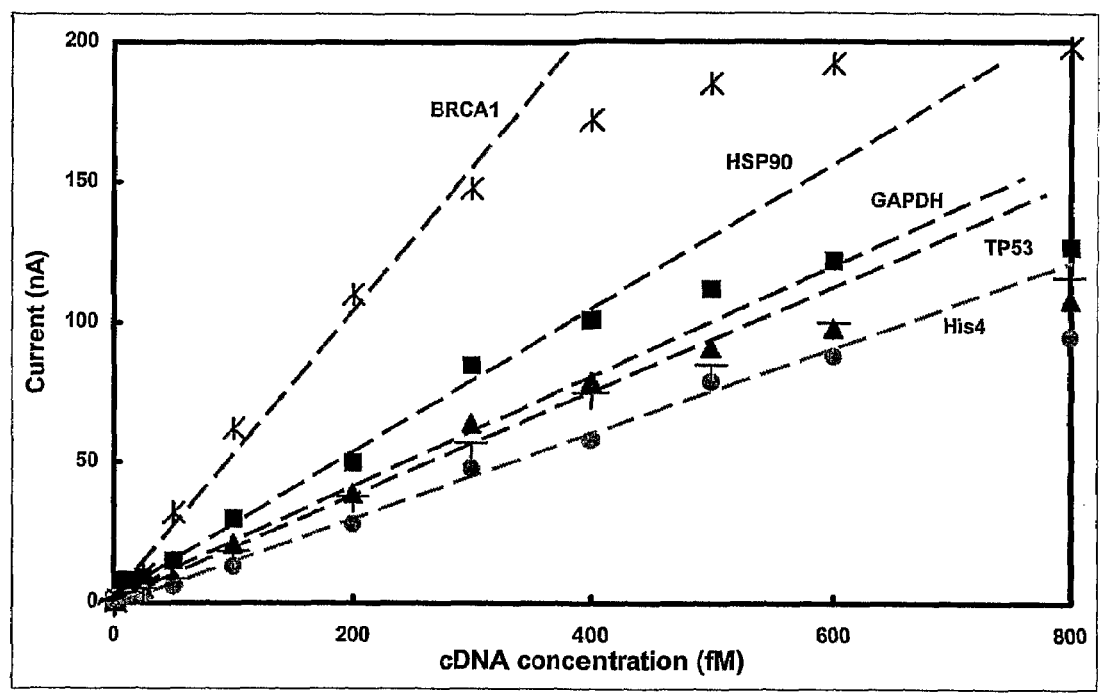
FIG. 9 Amperometric responses of breast cancer susceptibility genes at different concentrations. Conditions are the same as that for FIG. 7.

Since most of the breast cancers are in one way or another associated with breast cancer susceptibility genes categorized in four clusters, techniques that could offer sensitive detection and accurate quantification of these genes will help to facilitate earlier diagnosis and prognosis (Martin, K. J. et al. Cancer Res. 2000, 60, 2232). In this study, cisplatin labeled cDNAs were used as standards and diluted to different concentrations with TE buffer before use. Analyte solutions with different concentrations of cDNA, ranging from 0.10 fM to 2.0 pM, were tested. For the control experiments, non-complementary capture probes were used in the sensor preparation. As depicted in FIG. 9, the current increased linearly with the concentration of cDNA within this range. The dynamic ranges for TP53, HSP90, BRCA1, His4 and GAPDH were 2.0-400 fM, 2.0-400 fM, 1.0-300 fM, 2.0-600 μMd and 1.5-400 fM, with detection limits of 1.0, 1.0, 0.50, 2.0 and 1.0 fM, corresponding to 0.20, 0.45, 0.95, 0.10 and 0.27 fg, respectively. Taking the sample volume into consideration, as few as 800 copies of nucleic acid molecules were successfully detected using the proposed method. This appears to be the lowest reported amount of genomic nucleic acid detected electrochemically. Compared to previous results based on the sandwich-type assays (Patolsky, F., Lichtenstein, A., Kotler, M. & Willner, I. Angew. Chem. Int. Ed. 2001, 40, 2261; Drummond, T. G., Hill, M. G., & Barton, J. K. Nat. Biotechnol. 2003, 21, 1192) the sensitivity of genomic nucleic acid analysis was greatly improved by adopting the multiple enzyme labeling scheme and the result was comparable to that obtained with short synthetic oligonucleotides of 20-50 bases in length. In the sandwich-type assays reported earlier (Patolsky, F., Lichtenstein, A., Kotler, M. & Willner, I. Angew. Chem. Int Ed. 2001, 40, 2261; Drummond, T. G., Hill, M. G., & Barton, J. K. Nat. Biotechnol. 2003, 21, 1192), the ratio of enzyme label and target nucleic acid molecule was fixed at unit. The amount of capture probes immobilized on the sensor surface and hybridization efficiency determined the amount of target nucleic acid bound to the surface and thereby the amount of enzyme labels in spite of the size of the genes. In fact, much lower current sensitivity was observed for longer nucleic acid molecules. However, in the present proposed model, multiple cisplatin-biotin labels on a single nucleic acid chain greatly increased the enzyme label loading, corresponding responses from enzymatic reaction were increased accordingly, and hence the sensitivity and detection limit of the nucleic acid biosensor were substantially improved when working with real-world samples. For example, for a 1000 base long nucleic acid, if there is one enzyme label per 50 bases, the overall signal could increase by 20-fold. It was found that by labeling the nucleic acid molecules with multiple enzyme molecules, via the cisplatin-biotin conjugates, the sensitivity was increased by 15-40 fold compared to the sandwich-type assay, depending on the length of the gene. The sensitivity obtained in this work was comparable to that observed with the short synthetic oligonucleotide (50-mer) of the sandwich-type approaches (Patolsky, F., Lichtenstein, A., Kotler, M. & Willner, I. Angew. Chem. Int. Ed. 2001, 40, 2261; Drummond, T. G., Hill, M. G., & Barton, J. K. Nat. Biotechnol. 2003, 21, 1192), indicating that the enzyme/base ratio has very small variation for both short synthetic oligonucleotides and genomic nucleic acid samples, which, in turn, generated analytical signals of similar sensitivities. The enzyme label/base ratio was estimated to be in the range of 1/40-100 depending on the length of the nucleic acid molecules. Theoretically, if this ratio keeps unchanged for all genes, the same current sensitivity per base should be obtained for all genes. It was noteworthy that the sensitivity per base is, however, nucleic acid length-dependent. For example, the sensitivity for BRCA1 was more than doubled as compared to other genes, due to significantly more bases (5592 bp) in the gene. But in terms of current sensitivity per base, BRCA1 was the lowest. In principle, at the same molar concentration, the sensitivity should be roughly proportional to the number of bases in the gene, but this trend was not observed in the present experiments. It was found that His4 (312 bp), the shortest among the genes studied, had the highest current sensitivity per base. This was probably due to the fact that not all biotin moieties were equally accessible to GOx-A conjugates due to steric hindrance and three-dimensional packing of the nucleic acid molecules on the sensor surface. It would be much easier for GOx-A conjugates to interact with biotin moieties attached to shorter nucleic acid chain (shorter genes) since some of biotin moieties may be 'buried' deeply inside longer DNA molecules.

Detection of Breast Cancer Susceptibility Genes in Human Breast Tissues

Four representative breast cancer susceptibility genes, namely, TP53, HSP90, BRCA1, His4, plus a house-keeping gene GAPDH were tested on the sensor array after total mRNA was extracted from human breast tissues. Immediately following surgery, the breast tissue samples were stored in liquid nitrogen until mRNA extraction. Tissue was mechanically homogenized and total mRNA was extracted by means of magnetic beds extraction (a Dynabeads® mRNA DIRECT™ Kit; Dynal ASA, Oslo, Norway). A GAPDH cDNA of a RT-PCR product was used as internal control. The mRNA levels were quantified on the sensor array (10 duplicates for each gene and total 14 controls) and were calculated as ratios relative to the mRNA of the house-keeping gene GAPDH in normal tissues. As can be seen in Table 3, under-expression for BRCA1 and His 4 and overexpression for HSP90 were observed in breast cancer tissues, whereas TP53 showed little difference between cancer and normal tissues, due probably to the high probability of TP53 mutations, not expression changes in cancer tissues and the mutated TP53 gene was also captured by the sensor.

TABLE 3

Expression of TP53, HSP90, BRCA1, His4 and GAPDH in human breast tissues[1]

| | TPS3 | HSP90 | BRCA1 | His4 | GAPDH |
|---|---|---|---|---|---|
| Cancer Tissue[2] | 0.5 ± 0.16 | 1.78 ± 0.48 | 0.14 ± 0.05 | 0.16 ± 0.06 | 0.94 ± 0.23 |
| Normal Tissue[3] | 0.52 ± 0.16 | 0.36 ± 0.10 | 0.23 ± 0.06 | 0.31 ± 0.10 | 0.98 ± 0.24 |

Figure 10:
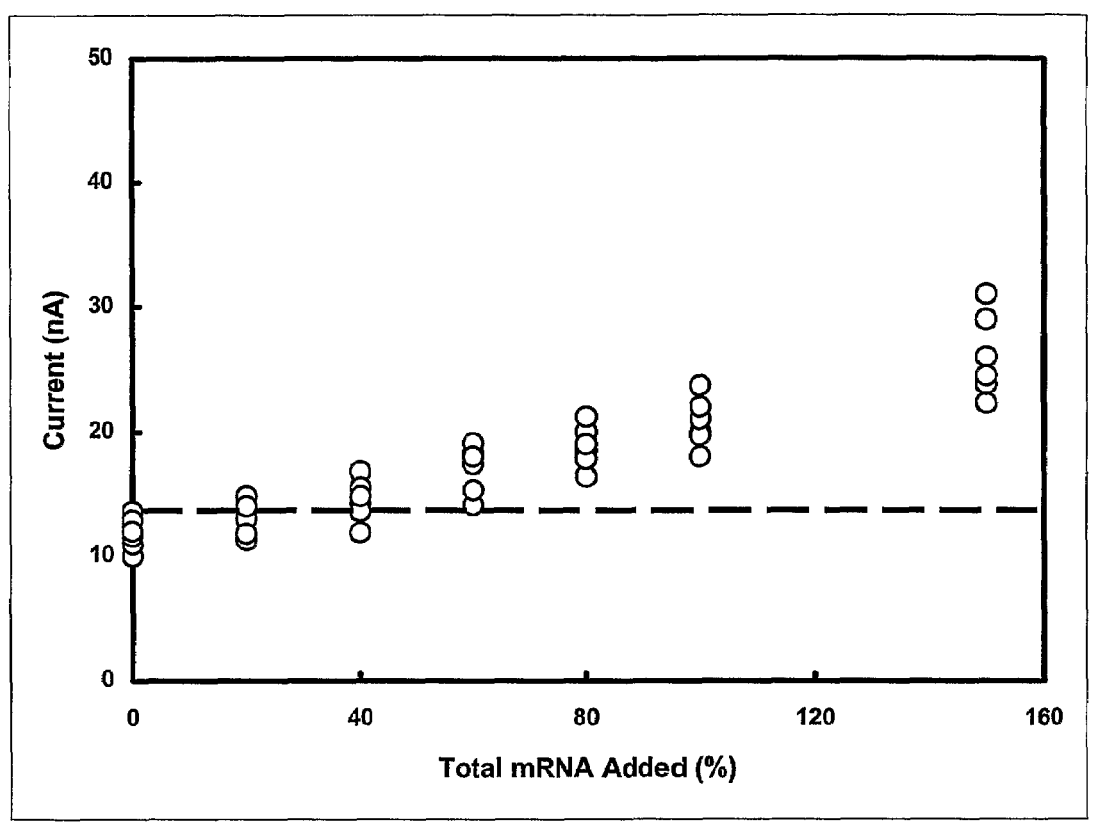
FIG. 10 Dependence of amperometric responses (6 duplicates) on TP53 mRNA expression levels. The expression levels were mimicked by adding various amounts of the total mRNA to a test solution containing 50 ng total mRNA. Conditions as for FIG. 7.

[1] mRNA expression was given as ratios relative to the GAPDR mRNA.
[2] Average of 8 breast cancer tissues.
[3] Average of 3 normal tissues These results are in good agreement with some earlier reports (30 Rosen, B. M.; fan, S.; Pestell, R. G.; Goldberg, L. D. J. Cell. Physiol. 2003, 19-41; Pavelic, K.; Gall-Troselj, K,; *J. Mol. Med.* 2001, 79, 566-573; Saad, Z.; Bramwell, V. H.; Wilson, S. M., O'Malley, F. P., Jeacock, J.; Chambers, A. F. *Lancet,* 1998, 351, 1170-1173. 33 Gullans, S. R. *Nature Genet.* 2000,26, 4-5). However, useful clinical information can only be drawn from a statistically valid number of samples in connection with patient's medical history. Nonetheless, these data confirm the applicability of the sensor array in direct analyzing real-world samples. The lowest amount of total mRNA needed for successful mRNA detections was found to be about 1.5 ng. Considering there are about 30000 genes in this total mRNA pool, the actual detectable limit for each specific mRNA is at sub-femtograms on average, which is in good agreement with the calibration study (see above). The relative errors associated with mRNA assays on individual genes were generally less than 25% in the concentration range of 2.0 to 300 fM. Therefore, it allowed for the identification of genes that differ less than 1-fold in expression between two conditions. It is very difficult to detect 2-fold different gene expression using current technology. One can only reliably discriminate gene expression differences of more than 3-fold (Saad, Z.; Bramwell, V. H.; Wilson, S. M., O'Malley, F. P., Jeacock, J.; Chambers, A. F. *Lancet,* 1998, 351, 1170-1173. 33 Gullans, S. R. *Nature Genet* 2000,26,4-5). But in many cases the expression of many of the most interesting genes may only differ a little between different conditions. To determine the ability in detecting minute changes in gene expression, multiple assays on TP53 mRNA in 50 ng total mRNA were performed. Expression levels of TP53 were mimicked by adding various amounts of the total mRNA to the test solution. FIG. 10 clearly shows that the proposed assay can unambiguously detect less than 1-fold gene expression difference. As can be seen in FIG. 10, amperometric response of TP53 was completely resolved from that of the test solution after adding 0.80-fold of the total mRNA to it. This allows a greater accuracy in the identification of differentially expressed genes at and cuts down on the need for running too many replicates. In addition, with the much improved sensitivity, at least 1000-fold more sensitive than those of fluorescence-based assays, the proposed method also significantly cuts down the amount of total mRNA from micrograms to nanograms.

CONCLUSIONS

The electrochemical sensor array described here is rapid, ultrasensitive, non-radioactive, based upon genomic mRNA and is able to directly detect breast cancer susceptibility genes and a house-keeping gene from the total mRNA extract without PCR amplification. By employing the cisplatin-biotin conjugate, mRNA was directly labeled with biotin moieties in a one-step non-enzymatic reaction. With the hybridization process and the formation of the mRNA+GOx-A/polymeric activator bilayer, specific genes were detected amperometrically with high sensitivity and specificity. By labeling mRNA sample with multiple enzyme molecules, the sensitivity was greatly increased by 15-40 fold compared to the sandwich-type assay. Full-length mRNAs of cancer susceptibility genes from human breast tissues were selectively detected at femtomolar levels using the 8×8 sensor array Less than 1-fold gene expression difference was successfully detected. The lowest detectable amount of mRNA was found to be around 800 copies in as little as 1.5 ng total mRNA. By integrating the sensor array into a fully automated microelectromechanical system, from tissue digestion and sample preparation to nucleic acid isolation and quantification, it will provide faster, cheaper and simpler solutions for molecular diagnosis, particularly for early cancer diagnosis, point-of-care and field uses.

The invention claimed is:

1. A method for the detection and/or quantification of at least one target nucleic acid or target polypeptide in a sample of nucleic acids or polypeptides comprising the steps of:
   (a) providing a sample comprising nucleic acids or polypeptides;
   (b) labeling the nucleic acids or polypeptides with a ligand conjugate, the ligand conjugate comprising a first element binding to the nucleic acids or polypeptides and a second element which is a capture ligand;
   (c) contacting the nucleic acids-ligand conjugate or polypeptides-ligand conjugate with at least one capture probe, the capture probe hybridizing with or binding to at least one target nucleic acid or target polypeptide;
   (d) adding i) an oxidoreductase enzyme, wherein the oxidoreductase enzyme is recognized by the capture ligand, or ii) a complex comprising an oxidoreductase enzyme bound to a capture receptor, the capture receptor capable of binding to the capture ligand;
   (e) adding a redox polymer, the redox polymer binding to the oxidoreductase enzyme, thereby resulting in the transfer of electrons from the enzyme via the redox polymer to an electrode surface; and
   (f) detecting and/or quantifying the presence of the target nucleic acid(s) or target polypeptide(s),
   wherein the first element binding to the nucleic acids or to the polypeptides is cisplatin, platinum-linked Cyanine 3, platinum-linked Cyanine 5, and the capture ligand is biotin, digoxigenin, an antibody or antigen binding to the capture receptor, an antibody binding to the oxidoreductase enzyme, an aptamer, a protein and/or a protein receptor.

2. The method of claim 1, wherein the capture probe is fixed onto an electrode surface or comprises capture probe fixing means for fixing the capture probe to an electrode surface.

3. The method of claim 1, wherein the capture probe is an oligonucleotide hybridizing with at least one portion of the target nucleic acid.

4. The method of claim 1, wherein the sample of nucleic acids or polypeptides is a sample of: (i) mRNAs; or (ii) mRNAs in combination with cDNAs and/or genomic DNA.

5. The method of claim 1, wherein the sample of nucleic acids or polypeptides is a sample of total mRNA and the capture probe hybridizes to at least one target mRNA.

6. The method of claim 1, wherein the capture probe is an antibody or a ligand binding to the target polypeptide.

7. The method of claim 1, wherein the sample of polypeptide is a sample of proteins and the capture probe binds to at least one target protein.

8. The method of claim 1, wherein the capture receptor is avidin, streptoavidin, anti-digoxigenin, an antigen or antibody binding to the capture ligand, an aptamer, a protein and/or a protein receptor.

9. The method of claim 1, wherein the oxidoreductase enzyme binds to the capture ligand, wherein the capture ligand is an antibody.

10. The method of claim 1, wherein the oxidoreductase enzyme is an oxidase, a dehydrogenase, a mono-oxygenase, a hydroxylase, a dioxygenase, a peroxidase, or a hydrogenase.

11. The method of claim 10, wherein the oxidase is glucose oxidase (GOX), lactase oxidase (LAX), pyruvate oxidase (PYX), tyrosinase, horseradish peroxidase (HRP), or a mixture thereof.

12. The method of claim 1, wherein the redox polymer is a redox active polymeric material, poly(vinylimidazole-co-acrylamide), poly(vinylimidazole-co-acrylamide) partially imidazole-complexed with [Os(bpy)$_2$], [Os(dmbpy)$_2$], [(Osbpy)$_2$(im)], [Os(dabpy)$_2$] and/or [Os(bpy)$_2$(Mim)], poly[vinylpyridine Os(bis-bipyridine)$_2$Cl-co-allylamine] (PVP-Os-AA), ferrocene-based polymer, and/or ruthenium-based polymers.

13. The method of claim 2, wherein the electrode surface is made of gold, platinum, glassy carbon, graphite, carbon pastes (CPE) or carbon-epoxy composites for amperometry.

14. The method of claim 1, wherein the method is a method for the direct detection and/or quantification of specific genes in total mRNA sample.

15. The method of claim 1, wherein the sample is a mammal sample.

16. The method of claim 1, wherein the sample is a human sample.

17. The method of claim 14, wherein the mRNA sample is extracted from a tissue.

18. The method of claim 1, wherein the ligand conjugate is cisplatin-biotin and the capture receptor is avidin or streptoavidin.

19. The method of claim 1, wherein the method is a diagnostic method for the detection and/or quantification of one or more target genes.

20. The method of claim 19, wherein the target gene is at least one of tumor protein p53 (TP53), heat-shock protein 90 (HSP90), breast cancer gene 1 (BRCA1), and Histone H4 (His4).

21. The method of claim 1, wherein detection limits of the at least one target mRNA are 0.20-1.0 fg.

22. The method of claim 1, wherein the target mRNA corresponds to the breast cancer gene 1 (BRCA1).

23. The method of claim 1, wherein the method is carried out on a sensor array.

24. The method of claim 23, wherein the sensor array comprises: a support; a first electrode material applied on the support; a spacer/insulator layer applied on the electrode material, and a second electrode material.

25. The method of claim 24, wherein the electrode material is made of gold, platinum, glassy carbon, graphite, carbon pastes (CPE) or carbon-epoxy composites for amperometry.

26. The method of claim 24, wherein the spacer/insulator layer comprises, from the bottom to the top, an adhesive spacing/insulating layer, a screen-printed Ag/AgCl layer and a hydrophobic layer.

27. The method of claim 24, wherein the support is a glass support.

28. The method of claim 1, wherein the method is integrated into a microelectromedical system (MEMS) and/or fully automated Micro Total Analysis System (µ-TAS).

29. The method of claim 1, wherein the sample of nucleic acids is a sample of cDNAs and/or genomic DNA and the capture probe hybridizes to at least one target cDNA or to at least one target genomic DNA fragment.

30. The method of claim 21, wherein the detected target nucleic acid is mRNA.

* * * * *

SEQUENCE LISTING

<160> NUMBER OF SEQ ID NOS: 9

<210> SEQ ID NO 1
<211> LENGTH: 20
<212> TYPE: DNA
<213> ORGANISM: Artificial
<220> FEATURE:
<223> OTHER INFORMATION: PCR primer

<400> SEQUENCE: 1
atggtgaagg tcggtgtcaa                                                     20

<210> SEQ ID NO 2
<211> LENGTH: 20
<212> TYPE: DNA
<213> ORGANISM: Artificial
<220> FEATURE:
<223> OTHER INFORMATION: PCR primer

<400> SEQUENCE: 2
ttactccttg gaggccatgt                                                     20

<210> SEQ ID NO 3
<211> LENGTH: 20
<212> TYPE: DNA
<213> ORGANISM: Artificial

```
<220> FEATURE:
<223> OTHER INFORMATION: PCR Primer

<400> SEQUENCE: 3
atggaggatt cacagtcgga                                              20

<210> SEQ ID NO 4
<211> LENGTH: 18
<212> TYPE: DNA
<213> ORGANISM: artificial
<220> FEATURE:
<223> OTHER INFORMATION: PCR primer

<400> SEQUENCE: 4
tcagtctgag tcaggccc                                                18

<210> SEQ ID NO 5
<211> LENGTH: 32
<212> TYPE: DNA
<213> ORGANISM: Artificial
<220> FEATURE:
<223> OTHER INFORMATION: Capture probe oligonucleotide

<400> SEQUENCE: 5
aaaaaaaaaa aaatggagga ttcacagtcg ga                                32

<210> SEQ ID NO 6
<211> LENGTH: 32
<212> TYPE: DNA
<213> ORGANISM: Artificial
<220> FEATURE:
<223> OTHER INFORMATION: Capture probe oligonucleotide

<400> SEQUENCE: 6
aaaaaaaaaa aatcagtctg agtcaggccc ca                                32

<210> SEQ ID NO 7
<211> LENGTH: 35
<212> TYPE: DNA
<213> ORGANISM: Artificial
<220> FEATURE:
<223> OTHER INFORMATION: Capture probe oligonucleotide

<400> SEQUENCE: 7
aaaaaaaaaa aattactcct tggaggccat gtagg                             35

<210> SEQ ID NO 8
<211> LENGTH: 35
<212> TYPE: DNA
<213> ORGANISM: Artificial
<220> FEATURE:
<223> OTHER INFORMATION: Capture probe oligonucleotide

<400> SEQUENCE: 8
aaaaaaaaaa aaatggtgaa ggtcggtgtc aacgg                             35

<210> SEQ ID NO 9
<211> LENGTH: 35
<212> TYPE: DNA
<213> ORGANISM: Artificial
<220> FEATURE:
<223> OTHER INFORMATION: Capture probe oligonucleotide

<400> SEQUENCE: 9
aaaaaaaaaa aacctctcgc gagtcaacag aaacg                             35
```